United States Patent
Chen et al.

(10) Patent No.: US 6,894,172 B2
(45) Date of Patent: May 17, 2005

(54) CHIRAL CHEATING AGENT AND CHIRAL CATALYST

(75) Inventors: Kwunmin Chen, Taipei (TW); Kung-Shou Yang, Taipei (TW); Wei-Der Lee, Kaohsiung (TW); Jia-Fu Pan, Changhua (TW)

(73) Assignee: National Taiwan Normal University, Taipei (TW)

( * ) Notice: Subject to any disclaimer, the term of this patent is extended or adjusted under 35 U.S.C. 154(b) by 6 days.

(21) Appl. No.: 10/612,609

(22) Filed: Jul. 1, 2003

(65) Prior Publication Data

US 2004/0176243 A1 Sep. 9, 2004

(30) Foreign Application Priority Data

Feb. 27, 2003 (TW) ........................ 92104138 A

(51) Int. Cl.[7] ................ C07D 275/06; C07C 233/57; C07C 69/74
(52) U.S. Cl. ................ 548/207; 548/208; 564/152; 560/126; 560/127; 502/15; 502/170; 502/200; 502/302
(58) Field of Search ................ 560/127, 128, 560/125; 548/207, 208; 564/152, 82; 502/15, 170, 200, 302; 562/509, 507

(56) References Cited

PUBLICATIONS

Carvalho et al, Inorganic Chem., vol. 33, pp. 6270–6277, 1994.*
Yang et al, Organic Letters, vol. 4, No. 7, 2002, pp. 1107–1109.*

* cited by examiner

Primary Examiner—Shailendra Kumar
(74) Attorney, Agent, or Firm—J.C. Patents

(57) ABSTRACT

Chiral chelating agents and chiral catalysts, which are formed from the chiral chelating agents and metal, are described. One chiral chelating agent has a general formula (1) as illustrated below:

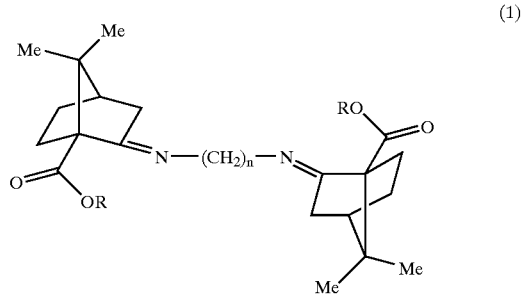

(1)

wherein R represents H, methyl, ethyl, a primary, secondary or tertiary straight, branched or cyclic alkyl group having 3–7 carbon atoms, a heterocyclic or aromatic group, an aromatic group substituted at the 2-, 3- or 4-position, an aromatic-like group, or a naphthyl or naphthyl-derived group, and n is an integer between 0 and 4.

4 Claims, No Drawings

CHIRAL CHEATING AGENT AND CHIRAL CATALYST

CROSS-REFERENCE TO RELATED APPLICATION

This application claims the priority benefit of Taiwan application serial no. 92104138, filed Feb. 27, 2003.

BACKGROUND OF THE INVENTION

1. Field of the Invention

The present invention relates to chiral cheating agents and chiral catlysts, wherein the chiral catlysts are formed from the chiral chelating agents and metals.

2. Background of the Invention

The use of catalytic asymmetric reactions for the synthesis of enantiomerically pure compounds has been an ongoing effort of organic chemists. The coupling of an α,β-unsaturated carbonyl/nitrile with an aldehyde (Morita-Baylis Hillman reaction) produces a useful functionalized acrylate that allows for further functional group manipulation. The reaction can be catalyzed by using a chiral catalyst to synthetize a product having high level of enantiomeric excess. The mechanism of the Baylis-Hillman reaction, which is mediated by a tertiary amine, is illustrated as follows:

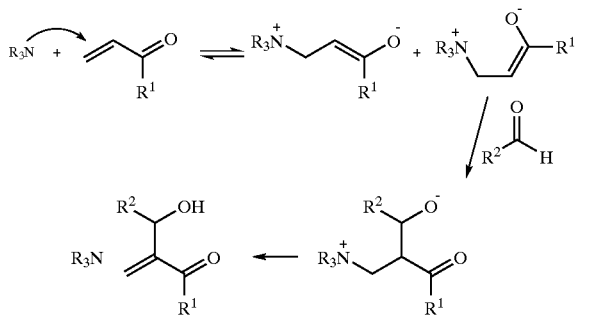

Although the diastereoselective Baylis-Hillman reaction has been shown to proceed, in some cases, with high to excellent diastereoselectivities, the enantioselective variation of this reaction is less well developed.

Recently, Hatakeyama et al. reported that a high to excellent enantiomeric excess can be achieved when quinidine derivatives are used as chiral amine catalysts (*J. Am. Chem. Soc.*, 1999, 121, 10219). The use of a chiral Lewis acid to catalyze this transformation is a common strategy. Aggarwal and co-workers report on the use of lanthanides and group III metal triflates to accelerate the Baylis-Hillman reaction (*J. Org. Chem.* 1998, 63, 7183 and *J Chem. Soc. Chem. Commun.,* 1996, 2713). However, only 5% ee was obtained, when these metals are complexed with a broad range of oxygen-rich chiral ligands. No practical levels of enantioselectivity have yet been reported when a chiral Lewis acid catalyst is used.

SUMMARY OF THE INVENTION

The present invention provides chiral chelating agents and chiral catlysts, which are formed from the chiral reagents and metals to improve the enantioselectivity of catalytic asymmetric reactions.

The present invention provides a chiral chelating agent, which is a campor derivative having a structure of any one of the formulas (1) to (17) and an enantiomeric or an diastereomeric isomer of any one of the formulas (1) to (17):

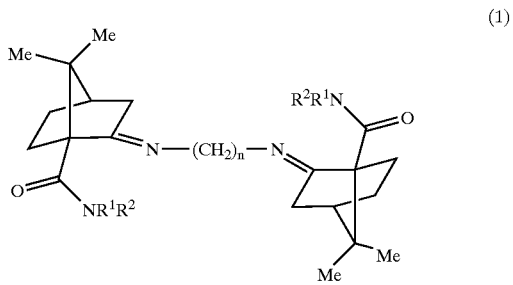

wherein $R^1$ and $R^2$ represent H, methyl, ethyl, a primary, secondary or tertiary straight, branched or cyclic alkyl group having 3–7 carbon atoms, a heterocyclic or aromatic group, an aromatic group substituted at 2-, 3- or 4-position, an aromatic-like group, or a naphthyl or naphthyl-derived group, and n is an integer between 0 and 4;

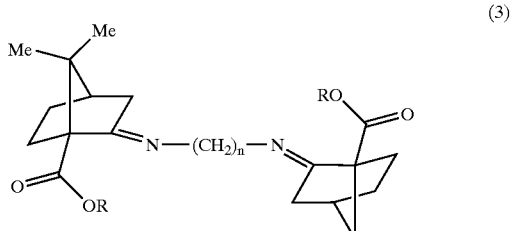

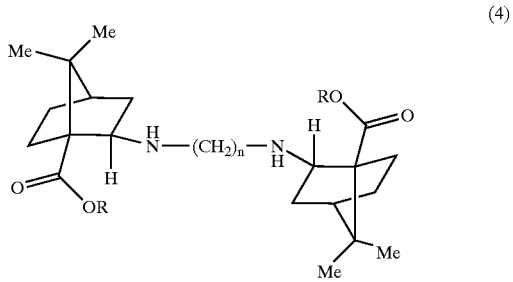

wherein R represents H, methyl, ethyl, a primary, secondary or tertiary straight, branched or cyclic alkyl group having 3–7 carbon atoms, a heterocyclic or aromatic group, an aromatic group substituted at 2-, 3- or 4-position, an aromatic-like group, or a naphthyl or naphthyl-derived group, and n is an integer between 0 and 4;

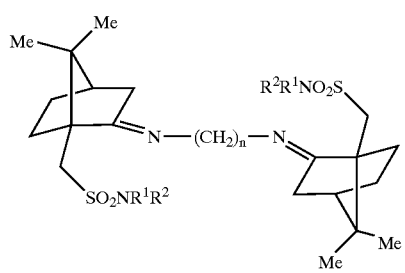

(5)

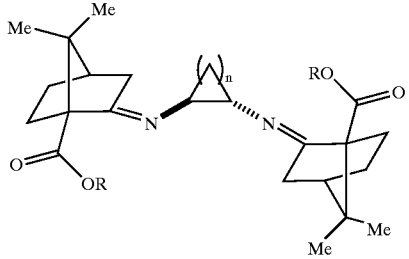

(9)

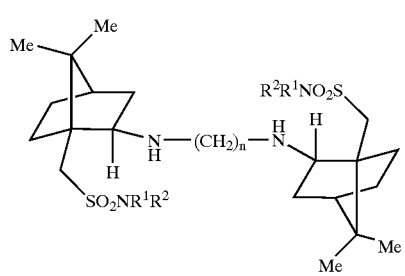

(6)

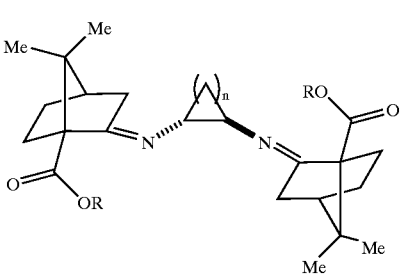

(10)

wherein $R^1$ and $R^2$ represent H, methyl, ethyl, a primary, secondary or tertiary straight, branched or cyclic alkyl group having 3–7 carbon atoms, a heterocyclic or aromatic group, an aromatic group substituted at 2-, 3- or 4-position, an aromatic-like group, or a naphthyl or naphthyl-derived group, and n is an integer between 0 and 4.

wherein R represents H, methyl, ethyl, a primary, secondary or tertiary straight, branched or cyclic alkyl group having 3–7 carbon atoms, a heterocyclic or aromatic group, an aromatic group substituted at 2-, 3- or 4-position, an aromatic-like group, or a naphthyl or naphthyl-derived group, and n is an integer between 0 and 4.

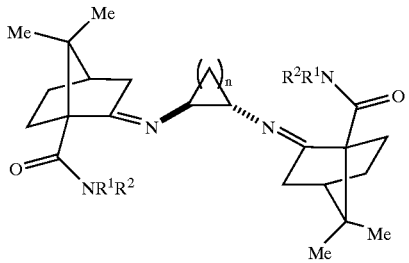

(7)

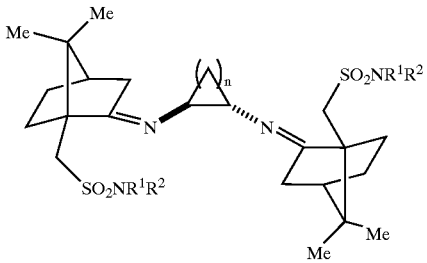

(11)

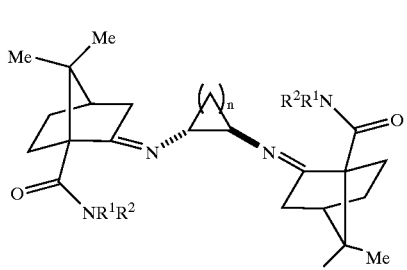

(8)

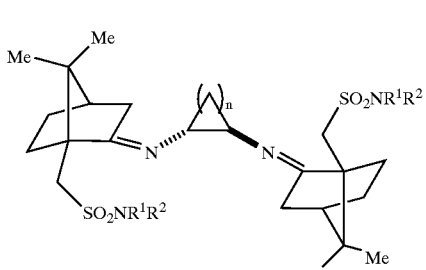

(12)

wherein $R^1$ and $R^2$ represent H, methyl, ethyl, a primary, secondary or tertiary straight, branched or cyclic alkyl group having 3–7 carbon atoms, a heterocyclic or aromatic group, an aromatic group substituted at 2-, 3- or 4-position, an aromatic-like group, or a naphthyl or naphthyl-derived group, and n is an integer between 0 and 4.

wherein $R^1$ and $R^2$ represent H, methyl, ethyl, a primary, secondary or tertiary straight, branched or cyclic alkyl group having 3–7 carbon atoms, a heterocyclic or aromatic group, an aromatic group substituted at 2-, 3- or 4-position, an aromatic-like group, or a naphthyl or naphthyl-derived group, and n is an integer between 0 and 4.

(13)

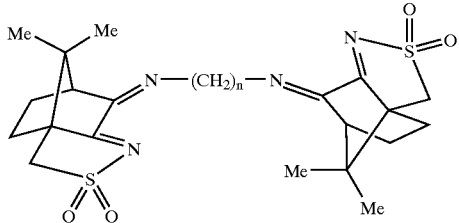

wherein n is an integer between 0 and 4.

(14)

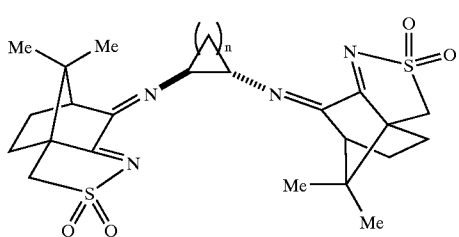

(15)

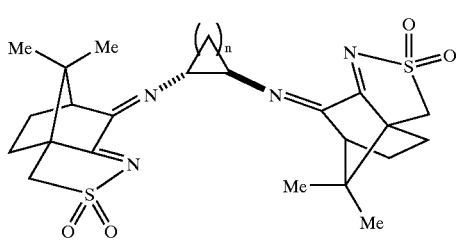

wherein n is an integer between 0 and 4.

(16)

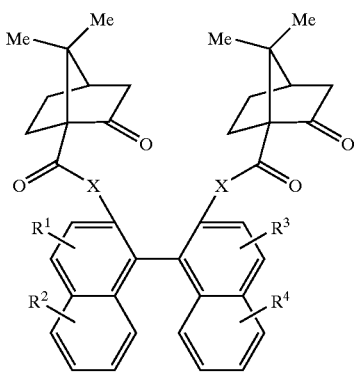

(17)

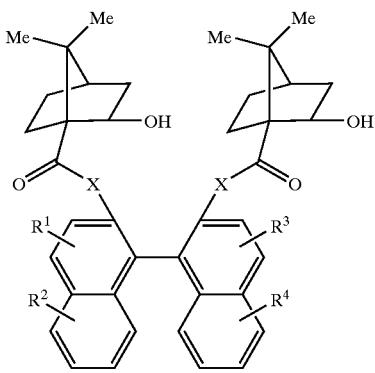

wherein X represents an oxygen atom or a nitrogen atom; $R^1$, $R^2$ $R^3$ and $R^4$ represent H, methyl, ethyl, a primary, secondary or tertiary straight, branched or cyclic alkyl group having 3–7 carbon atoms, a heterocyclic or aromatic group, an aromatic group substituted at 2-, 3- or 4-position, an aromatic-like group, a naphthyl or naphthyl-derived group or the above groups substituted with at least one halogen.

In addition, the chiral chelating agents of this invention comprise the diastereomers of the formulas (16) and (17).

The present invention provides a chiral catalyst, which is formed from the chiral chelating agent of any one of the above formulas (1) to (17) and a metal, wherein the metal comprises an alkali metal, an alkaline earth metal or a transition metal including a lanthanide metal.

The chiral catalyst of this invention is suitable for use in a Baylis-Hillman reaction. In some cases, the enantiomeric excess of the product is determined to be 71%. This represents that the chiral catalysts of this invention improve the enantioselectivity of catalytic asymmetric reactions.

It is to be understood that both the foregoing general description and the following detailed description are exemplary, and are intended to provide further explanation of the invention as claimed.

DESCRIPTION OF THE PREFERRED EMBODIMENTS

The chiral chelating agents used in this embodiment comprise four agents, and the chiral catlysts used in this embodiment are formed from the four agents and lanthanide metals. The four agents is selected from the chiral chelating agents as illustrated above in formulas (3), (9) and (10), wherein the structures of the chiral chelating agent 1 and 4 are the above formulas (3) when R is H, and n is 2 and 0, respectively. The structures of the chiral chelating agent 2 and 3 are the above formulas (9) and (10) when R is H, and n is 4, respectively.

1

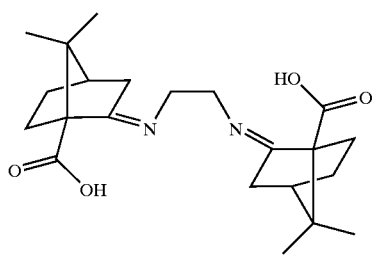

-continued

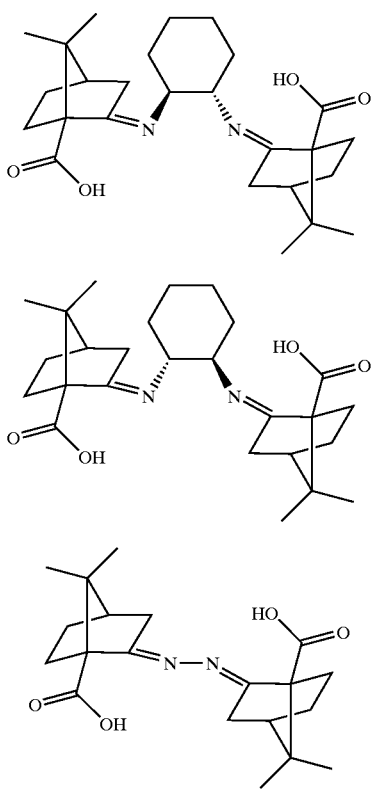

The four chiral chelating agents are prepared from the condensation of (+)-ketopinic acid with the corresponding diamines or hydrazine under acidic conditions. The chiral chelating agents 1 and 4 can be easily synthesized using ethylenediamine and hydrazine in the presence of acetic acid, and the yields are 69% and 88%, respectively. The chiral chelating agents 2 and 3 are provided by treatment of racemic trans-1,2-diaminocyclohexane with (+)-ketopinic acid in refluxing $CHCl_3$ for 36 hours. That the chiral chelating agents 2 and 3, which are diastereomers, can be separated by flash column chromatography and the absolute stereochemistry of the chiral chelating agents 3 is further confirmed by single crystal X-ray analysis.

The chiral chelating agent 1 is produced as follows: first, ethylenediamine (1.64 g, 27.4 mmol) and acetic acid (0.1 mL) is added into a solution of (+)-ketopinic acid (10 g, 54.9 mmol) in $CHCl_3$ (100 mL) at room temperature. The resulting mixture is then refluxed for 36 hours and the reaction then quenched with $H_2O$ (50 mL). The resulting solution is extracted with $CH_2Cl_2$ (100 mL) and the layers are separated. The organic layer is washed with brine (10 mL), dried ($MgSO_4$) and concentrated. The crude product is purified by silica gel using $EtOAc/CH_2Cl_2$ as the effluent (4/1) to give 7.22 g (69%) of the chiral chelating agent 1 as a white solid. The product is analyzed and the data is as follows:

$^1$H NMR (CDCl3, 200 MHz) δ3.65 (dd, J=15.0, 3.8 Hz, 4H), 2.56 (dd, J=18.2, 3.6 Hz, 2H), 2.40 (td, J=12.2, 3.6 Hz, 2H), 2.15–1.97 (m, 6H), 1.68 (td, J=12.8, 4.0 Hz, 2H), 1.43–1.30 (m, 2H,), 1.25 (s, 6H), 0.87 (s, 6H); $^{13}$C NMR (CDCl$_3$, 50 MHz) δ185.09, 173.21, 60.68, 50.78, 50.30, 43.86, 35.40, 31.62, 27.84, 20.07, 19.85; MS m/z (relative intensity) 388 (M$^+$, 8), 373 (10), 319 (100), 163 (23), 148 (30); HRMS m/z 388.2336 (calcd for $C_{22}H_{32}N_2O_4$ 388.2362).

The chiral chelating agent 2 and 3 are produced approximately the same way as above-mentioned except racemic trans-1,2-diaminocyclohexane having an optimum amount is in place of ethylenediamine. The products are analyzed and the data is as follows:

The Chiral Chelating Agent 2
$^1$H NMR (CDCl$_3$, 200 MHz) δ 3.45 (m, 2H), 2.52 (m, 2H), 2.36 (m, 2H), 2.11–1.98 (m, 6H), 1.81–1.67 (m, 4H), 1.60–1.24 (m, 6H), 1.22 (s, 6H), 0.86(s, 6H); $^{13}$C NMR (CDCl$_3$, 50 MHz) 67 183.34, 173.13, 64.38, 60.19, 50.37, 43.68, 34.99, 31.77, 30.54, 27.84, 23.76, 20.04, 19.57; and HRMS m/z 442.2834 (calcd for $C_{22}H_{32}N_2O_4$ 388.2362).

The Chiral Chelating Agent 3 $^1$H NMR (CDCl$_3$, 200 MHz) δ3.43 (dd, J=5.2, 3.2 Hz, 2H), 2.61 (t, J=3.0 Hz, 1H), 2.54 (t, J=3.8 Hz, 1H), 2.35 (td, J=12.1, 4.6 Hz, 2H), 2.11–1.92 (m, 6H), 1.83 (d, J=6.6 Hz, 2H), 1.65–1.27 (m, 10H), 1.25–1.24 (m, 2H), 1.23 (s, 6H), 0.83 (s, 6H); $^{13}$C NMR (CDCl$_3$, 50 MHz) δ183.24, 173.10, 64.33, 60.55, 49.31, 43.93, 34.93, 32.41, 31.07, 27.90, 23.85, 20.17, 20.06; MS m/z 442 (M$^+$, 7), 262 (35), 217 (50), 148 (45), 81 (100); HRMS m/z: 442.2833 (calcd for $C_{22}H_{32}N_2O_4$ 388.2362); and Crystal data at 22° C.: $C_{26}H_{38}N_2O_4$ M442.59, tetragonal, P4$_3$2$_1$2, a=7.8028(13) Å, c=40.282(4) Å, V=2452.5 Å$^3$, Z=4, λ=0.70930 Å, F(000)=960.56, Dc=1.199 Mg/m$^3$, μ=0.08 mm$^{-1}$, 5242 reflections, 146 parameters, R=0.051, and R$_w$=0.067 for all data.

The chiral chelating agent 4 is produced approximately the same way as above-mentioned except hydrazine is in place of ethylenediamine and $CH_2Cl_2$ is in place of $CHCl_3$. The products are analyzed and the data is as follows:

$^1$H NMR (CDCl$_3$, 200 MHz) δ 2.86 (t, J=3.6 Hz, 1H), 2.74 (t, J=3.8 Hz, 1H), 2.53 (td, J=12.6, 4.8 Hz, 2H), 2.32–2.04 (m, 6H), 1.82 (td, J=9.0, 4.2 Hz, 2H), 1,45 (m, 2H), 1.29 (s, 6H), 0.98 (s, 6H); $^{13}$C NMR (CDCl3, 50 MHz) δ181.90, 171.84, 60.99, 51.74, 44.03, 35.63, 31.65, 27.69, 20.01, 19.89; MS m/z 360 (M$^+$, 10), 316 (40), 288 (60), 163 (75), 148 (100), 134 (80), 95 (90); HRMS m/z 360.2011 (calcd for $C_{22}H_{32}N_2O_4$ 388.2362) Crystal data at 22° C.: $C_{20}H_{28}N_2O_4$ M 360.45, monoclinic, C2, a=11.414(3) Å, b=7.580(4) Å, c=21.887(3) Å, V=1865.4 Å$^3$, Z=4, λ=0.70930 Å, F(000)=776.48, D$_c$=1.283 Mg/m$^3$, μ=0.09 mm–1, 1812 reflections, 235 parameters, R=0.042, and R$_w$=0.079 for all data.

The lanthanide metal triflates were screened with the synthesized chiral chelating agents 1–4 using benzaldehyde and methyl acrylate (A), i.e. Baylis-Hillman reaction as model probes.

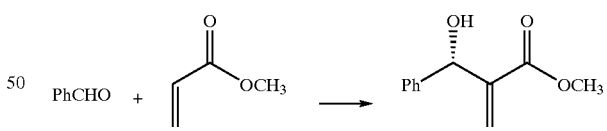

The catalytic system used in this case has a number of appealing features, which include (i) the molar ratio of chiral ligand to metal salts is designated to be 2:1 so that optimum enantioselectivity could be obtained under such conditions, deviation in either direction led to a decrease in selectivity (data not shown); (ii) a catalytic amount of catalyst (3 mol % of metal) is sufficient for asymmetric induction; (iii) the complexes are completely soluble in $CH_3CN$, giving a homogeneous solution in that ratio; and (iv) to prevent the formation of potential amine-Lewis acid complexes and therefore weaken the nucleophilic ability, a strictly controlled amount of 1,4-diazabicyclo[2.2.2] octane (DABCO) (10 equiv to the catalyst or 30 mol % to substrate) is used. The result is shown in Table 1 as follows:

TABLE 1

Reaction of benzaldehyde and methyl acrylate[a]

| entry | ligand | Lewis acid | yield (%)[b] | % ee[c] | configuration[d] |
|---|---|---|---|---|---|
| 1 | 1 | Eu(OTf)3 | 81 | 0 | S |
| 2 | 1 | Yb(OTf)3 | 72 | 17 | S |
| 3 | 1 | La(OTf)3 | 75 | 84 | S |
| 4 | 2 | La(OTf)3 | 70 | 67 | S |
| 5 | 3 | La(OTf)3 | 71 | 11 | S |
| 6 | 4 | La(OTf)3 | 0 | — | — |

[a]Benzaldehyde (0.5 mmol) is reacted with methyl acrylate A (0.5 mmol) in the presence of DABCO (30 mol %), Lewis acid catalyst (3 mol %) in CH3CN (2.6 mL) at room temperature for 10 hours.
[b]Isolated yield,
[c]Determined by HPLC analysis using a chiral column,
[d]Determined by comparison of optical rotation with the literature value.

From Table 1, it can be realized that the enantioselectivity is maximum when La is used as a lanthanide metal and the chiral chelating agent 1 is used as a ligand (entry 3).

To further determine the feasibility of the catalytic system, a variety of α,β-unsaturated carbonyl compounds with suitable aldehydes are studied under optimized conditions. A variety of acrylates with diverse steric, geometric, and electronic properties are surveyed in this transformation. These include methyl acrylate (A), t-butyl acrylate (B), phenyl acrylate (C), benzyl acrylate (D), and α-naphthyl acrylate (E). The reaction formula is as follows:

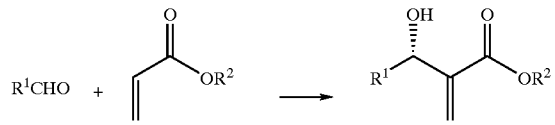

A: $R^2=CH_3$; B: $R^2=C(CH_3)_3$; C: $R^2=Ph$; D: $R^2=Bn$; and E: $R^2=\alpha$-Naphthyl The detail steps of the reaction of benzaldehyde and methyl acrylate are described as follows: first, the chiral cheating agent 1 (0.10 g, 0.26 mmol) is dissolved in $CH_3CN$ (2.6 mL), and then $La(OTf)_3$ is added at room temperature. The solution is stirred for 10 min and methyl acrylate (0.22 g, 2.60 mmol), benzaldehyde (0.27 g, 2.60 mmol) and DABCO (0.10 g, 0.78 mmol) are added sequentually. The resulting mixture is stirred for 20 min and the reaction is then quenched with $H_2O$ (5 mL). The resulting solution is extracted with $CH_2Cl_2$ (10 mL) and the layers are separated. The organic layer is washed with brine, dried with $MgSO_4$ and concentrated. The crude product is purified by silica gel using hexane/EtOAc as the eluent (8/1) to give 0.42 g (88%) of the Baylis-Hillman adduct with 84% ee. The product is analyzed and the data is as follows:

$[\alpha]_D=+93.3°$(c 1.0, $CHCl_3$); lit.$[\alpha]_D=-111.1°$ (c 111.1MeOH), for R enantiomer; $^1$H NMR ($CDCl_3$, 200 MHz) δ 7.38–7.26 (m, 5H), 6.32 (d, 1H, J=1.0 Hz), 5.85 (d, 1H, J=1.0 Hz), 5.40 (s, 1H), 3.69 (1, 3H), 3.13 (bs, 1H); $^{13}$C NMR ($CDCl_3$, 50 MHz) δ 1.66.71, 142.06, 141.32, 128.33, 127.72, 126.57, 125.85, 72.89, 51.72; HRMS m/z 192.0777 (calcd for $C_{11}H_{12}O_3$ 192.0786); and HPLC condition: 2-propanol:hexane=20:80 (0.5 mL/min), $t_R$=13.3 min (S) and 15.3 min (R).

The detailed steps of the reaction of benzaldehyde and α-naphthyl acrylate are described as follows: first, a solution of chiral ligand 1 (12 mg, 0.03 mmol) in $CH_3CN$ (2.6 mL) is added $La(OTf)_3$ (9 mg, 0.015 mmol) at room temperature under $N_2$ atmosphere. The solution is stirred for 10 min and benzaldehyde (54 mg, 0.51 mmol), α-naphthyl acrylate (0.10 g, 0.51 mmol) and DABCO (17 mg, 0.15 mmol) are added sequentually. The resulting mixture is stirred for 20 min and quenched with $H_2O$ (5 mL). The resulting solution is extracted with $CH_2Cl_2$ (10 mL) and the layers are separated. The organic layer is washed with brine (10 mL), dried ($MgSO_4$) and concentrated. The crude product is purified by silica gel using hexane/EtOAc as eluent (8/1) to give 0.13 g (88%) of product as a white solid. The enantiomeric ratios were determined by HPLC analyses using a chiral column. The result is shown in Table 2 as follows:

TABLE 2

Reaction of acrylates A–E with aldehydes catalyzed by $La(OTf)_3$ complexes[a]

| entry | acrylate | $R_1CHO(R_1=)$ | reaction time/hour | yield (%)[b] | configuration | (% ee)[c] |
|---|---|---|---|---|---|---|
| 1 | A | $CH_3$ | 10 | 85 | S | 10 |
| 2 | A | $CH_3CH_2$ | 10 | 89 | S | 7 |
| 3 | A | $(CH_3)_2CH$ | 10 | 75 | S | 6 |
| 4 | A | $4$-$MeOC_6H_4$ | 10 | 55 | S | 66 |
| 5 | B | Ph | 10 | 25 | S | 70 |
| 6 | C | Ph | 10 | 97 | S[d] | 75 |
| 7 | D | $CH_3$ | 10 | 85 | S | 65 |
| 8 | D | $CH_3CH_2$ | 10 | 85 | S | 65 |
| 9 | D | Ph | 10 | 75 | S[d] | 75 |
| 10 | D | $4$-$MeOC_6H_4$ | 10 | 50 | S | 95 |
| 11 | D | $4$-$NO_2C_6H_4$ | 10 | 93 | S | 85 |
| 12 | E | $c$-$C_6H_{11}$ | ⅓ | 71 | S | 71[e] |
| 13 | E | $CH_3CH_2$ | ⅓ | 75 | S | 70[f] |
| 14 | E | Ph | ⅓ | 88 | S[d] | 81 |
| 15 | E | $4$-$MeOC_6H_4$ | ⅓ | 35 | S | 95 |
| 16 | E | $4$-$NO_2C_6H_4$ | ⅓ | 82 | S | 93 |
| 17 | E | $Ph(CH_2)_2CH_2$ | ⅓ | 78 | S | 81 |

[a]All reactions are carried out at room temperature.
[b]Isolated yield.
[c]Determined by HPLC analysis using a chiral column.
[d]The absolute stereochemistry is determined by HPLC analysis after conversion to known product 5A ($R^1$ = Ph, $R^2$ = $CH_3$). The absolute stereochemistry of other products are assigned by analogy,
[e,f]% Ee is determined by conversion to the corresponding ester 5A ($R^1$ = $c$-$C_6H_{11}$, $R^2$ = $CH_3$) for HPLC analysis.

>From Table 2, it can be realized that the levels of asymmetric induction diminish appreciably when aliphatic aldehydes are treated with methylacrylate under the catalytic conditions employed (Table 2, entries 1–3). Good selectivity is obtained with low chemical yield when t-butyl acrylate was used with benzaldehyde (entry 5). Excellent chemical yield with moderate stereoselectivity was obtained when phenyl acrylate (C) was treated with benzaldehyde (entry 6).

Moreover, from Table 2, it can be realized that the stereoselectivity is remarkably enhanced when benzyl acrylate (D) was reacted with various aldehydes. A significant improvement in stereoselectivity was obtained when aliphatic aldehydes are reacted with benzyl acrylate (compare entries 1, 2 and 7, 8). The use of aromatic aldehydes with either electron donating or deficient substituents on the benzene ring gave high stereoselectivity (entries 10, 11). The use of benzylacrylate to provide good to high levels of stereoselectivity in the Baylis-Hillman products is interesting. However, the reaction requires 10 hours at room temperature for completion.

In addition, referring to entries 12 to 17 of Table 2, when α-naphthyl acrylate (E) serves as α,β-unsaturated carbonyl compound, the reaction time is reduced substantially. This represents that the reaction rate is remarkably enhanced. For example, treatment of the cyclohexanecarboxaldehyde with α-naphthyl acrylate afforded the desired product in 71% yield in 20 rain (entry 12). The enantioselectivity was determined to be 71% ee. In the case of aromatic aldehydes, high levels of stereoselectivities were obtained under the same reaction conditions (entries 14–16). The addition of ammonium enolate to an aldehyde is thought to be the rate-determining step of the Baylis-Hillman reaction. The remarkable rate acceleration using ammonium enolate can be attributed to the potential π-charge stabilization of the intermediates between the naphthalene aromatic system with the azaenolate. Stabilization of the ammonium enolate enhances the addition of DABCO to the α-naphthyl acrylate and therefore accelerates the reaction rates. The proposed mechanism of the enantioselective Baylis-Hillman reaction is illustrated as follows:

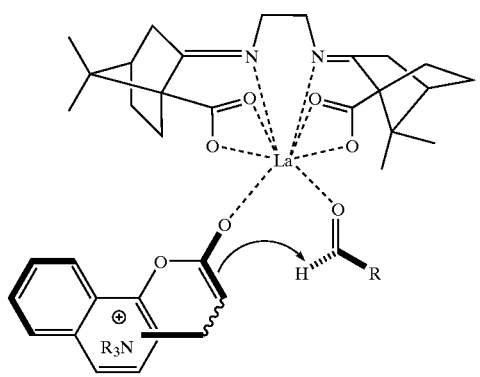

In conclusion, using the chiral catalysts of this invention catalyzing an asymmetric Baylis-Hillman reaction, a high level of enanfioselectivities can be obtained. Maximun enanfioselectivities can be obtained using 3 mol % of catalyst. In addition, when α-naphthyl acrylate is used as a Michael acceptor, the reaction is complete within 20 rain, in reasonable chemical yields and enantiomeric excess.

It would be understood to those skilled in the art that applications of the chiral catalyst of the present invention are not limited to the asymmetric Baylis-Hillman reaction. The chiral catalyst of the present invention can be applied in other chemical reactions, for example, a chiral alkylation, a chiral reduction, a chiral cyclization including a [2+2], a [3+2], a [4+2] or a [2+2+2] cyclization, a chiral hydrogenation, a chiral epoxidation, a chiral cyclization of propane, a chiral aziridination, a alkylation, a chiral dialkylation, a chiral hyroxyamination, a chiral amination, an Aldol reaction or a Michael addition reaction.

It will be apparent to those skilled in the art that various modifications and variations can be made to the structure of the present invention without departing from the scope or spirit of the invention. In view of the foregoing, it is intended that the present invention covers modifications and variations of this invention provided they fall within the scope of the following claims and their equivalents.

What is claimed is:

1. A chiral chelating agent having a formula (13) as follows and an enantiomeric isomer thereof:

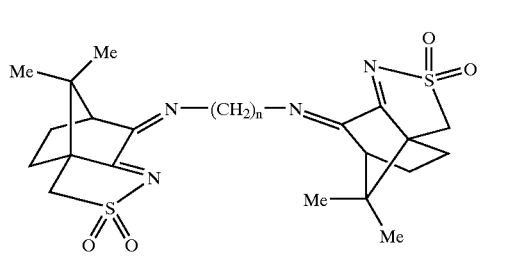

(13)

wherein n is an integer between 0 and 4.

2. A chiral chelating agent having a formula (14) as follows and an enantiomeric isomer thereof:

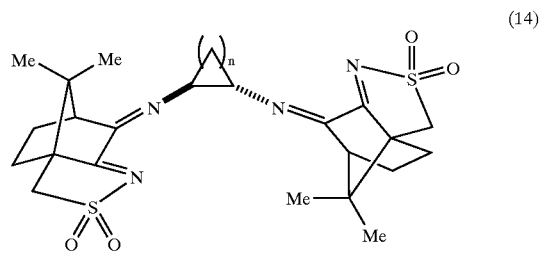

(14)

wherein n is an integer between 0 and 4.

3. A chiral chelating agent having a formula (15) as follows and an enantiomeric isomer thereof:

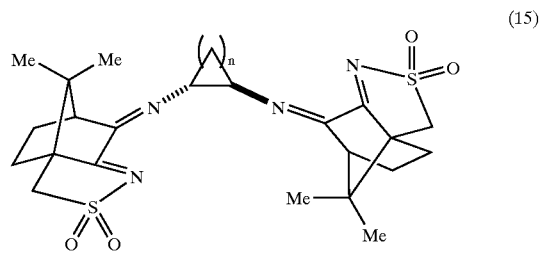

(15)

wherein n is an integer between 0 and 4.

4. A chiral chelating agent having a formula (16) as follows and a diastereomeric or an enantiomeric isomer thereof:

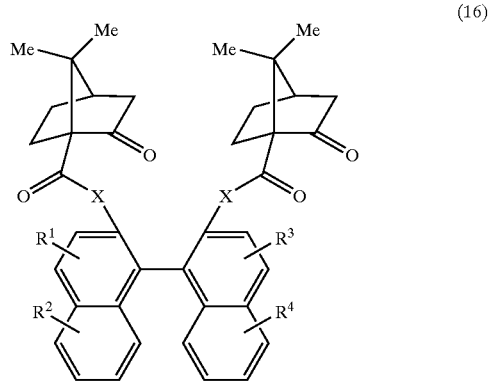

(16)

wherein X represents an oxygen atom or a nitrogen atom; $R^1$, $R^2$ $R^3$ and $R^4$ represent H, methyl, ethyl, a primary, secondary or tertiary straight, branched or cyclic alkyl group having 3–7 carbon atoms, a heterocyclic or aromatic group, an aromatic group substituted at the 2-, 3- or 4-position, an aromatic-like group, a naphthyl or naphthyl-derived group or the above groups substituted with at least a halogen.

* * * * *